United States Patent
Sakamoto et al.

(10) Patent No.: US 6,794,171 B2
(45) Date of Patent: Sep. 21, 2004

(54) D-PANTOLACTONE HYDROLASE AND GENE ENCODING THE SAME

(75) Inventors: Keiji Sakamoto, Takaoka (JP); Hideaki Yamada, Kyoto (JP); Sakayu Shimizu, Kyoto (JP); Michihiko Kobayashi, Kyoto (JP)

(73) Assignee: Fuji Yakuhin Kogyo Kabushiki Kaisha, Takaoka (JP)

(*) Notice: Subject to any disclaimer, the term of this patent is extended or adjusted under 35 U.S.C. 154(b) by 0 days.

(21) Appl. No.: 10/133,372

(22) Filed: Apr. 29, 2002

(65) Prior Publication Data

US 2003/0124697 A1 Jul. 3, 2003

Related U.S. Application Data

(62) Division of application No. 08/836,047, filed as application No. PCT/JP96/02620 on Sep. 13, 1996, now Pat. No. 6,406,898.

(30) Foreign Application Priority Data

Sep. 13, 1995 (JP) ............................................. 7-259451

(51) Int. Cl.[7] ........................... C12N 9/14; C12N 15/00; C12N 1/20; C12P 7/26; C07H 21/04
(52) U.S. Cl. ................. 435/195; 435/252.3; 435/320.1; 435/71.1; 435/148; 536/23.2
(58) Field of Search ............................... 435/195, 252.3, 435/320.1, 71.1, 148; 536/23.2

(56) References Cited

U.S. PATENT DOCUMENTS 5,275,949 A    1/1994   Sakamoto et al.
5,372,940 A   12/1994   Sakamoto et al.

FOREIGN PATENT DOCUMENTS

| EP | 0 436 730 | 7/1991 |
|---|---|---|
| EP | 0 504 421 | 9/1992 |
| JP | 55072182 | 5/1980 |
| JP | 62294092 | 12/1987 |
| JP | 62294094 | 12/1987 |
| JP | 62294096 | 12/1987 |
| JP | 4-144681 | 5/1992 |
| WO | WO 92/06182 | 4/1992 |

OTHER PUBLICATIONS

Fontana et al., Practical Protein Chemistry—A Handbook, A. Darbre, ed., pp. 67–120, 1986.
Lee et al., Science, vol. 239, pp. 1288–1291, Mar. 1988.
Amann et al., Gene, vol. 69, pp. 301–315, Mar. 1988.
Alberts et al., The Molecular Biology of The Cell, $3^{rd}$ Edition, pp. 608–609 and p. 455, 1995.
Sambrook et al., "Molecular Cloning", A Laboratory Manual, $2^{nd}$ Edition, Cold Spring Harbor Laboratory Press, p. 16.3, 1989.
Wiley et al., Practical Protein Chemistry—A Handbook, A Wiley—Interscience Publication, pp. 68–120, 1986.

*Primary Examiner*—Ponnathapu Achutamurthy
*Assistant Examiner*—Yong Pak
(74) *Attorney, Agent, or Firm*—Foley & Lardner LLP

(57) ABSTRACT

A novel enzyme which is useful in the optical resolution of D,L-pantolactone via D-selective asymmetric hydrolysis and a gene encoding the the same are provided. The invention discloses the gene coding for a natural D-pantolactone hydrolase (for example, one originating in *Fusarium oxysporum*) or proteins having an activity substantially equivalent thereto; host cells transformed with DNA containing a nucleotide sequence coding for said protein, processes for producing said protein via using said host cells and uses of said proteins and host cells.

11 Claims, 5 Drawing Sheets

| Peptide Number | Amino Acid Sequence |
|---|---|
| N-terminal | A K L P S T A Q I I D Q K S F N V L K D V P P P A V A ★ D S |
| No.1 | Q D E V K |
| No.2 | E A D A V R K |
| No.3 | L I G K |
| No.4 | L Y D |
| No.5 | S S I I Q K |
| No.6 | I S L K |
| No.7 | G R M I X T G Q T K |
| No.8 | L P S T A Q I I D Q K |
| No.9 | S F N V L K |
| No.10 | V T V V D S N P Q V I N P N G G T Y Y K |
| No.11 | G R V Y A G X G D G V H V W N P S G K |
| No.12 | I Y T G T V A A N F Q F A G K |
| No.13 | L F Y V T L G A S G P K |
| No.14 | T F A Y V A S F I P D G V H T D S K |
| No.15 | P F H V Y D E E F Y D V I G K |
| No.16 | V Y V T D T G I A L G F Y G R ★ L S S P A S V Y S F D V N Q D G T L Q N R K |
| No.17 | D V P P P A V A ★ D S L V F T (W) P G V T E E S L V E K |
| No.18 | D P S L T L I A T S D T D P I F H E A V V W Y P P T E(E) V F F V Q N A G A P A A G T G L ★ K |
| No.19 | G N I I F A G E G Q G D D V P S A L Y L M N P L P (P) Y ★ T T T L X ---- |

★ : N residue glycosylated    X : Uncertain residue

| Peptide Number | Amino Acid Sequence |
|---|---|
| N-terminal | A K L P S T A Q I I D Q K S F N V L K D V P P P A V A ★ D S |
| No.1 | Q D E V K |
| No.2 | E A D A V R K |
| No.3 | L I G K |
| No.4 | L Y D |
| No.5 | S S I I Q K |
| No.6 | I S L K |
| No.7 | G R M I X T G Q T K |
| No.8 | L P S T A Q I I D Q K |
| No.9 | S F N V L K |
| No.10 | V T V V D S N P Q V I N P N G G T Y Y K |
| No.11 | G R V Y A G X G D G V H V W N P S G K |
| No.12 | I Y T G T V A A N F Q F A G K |
| No.13 | L F Y V T L G A S G P K |
| No.14 | T F A Y V A S F I P D G V H T D S K |
| No.15 | P F H V Y D E E F Y D V I G K |
| No.16 | V Y V T D T G I A L G F Y G R ★ L S S P A S V Y S F D V N Q D G T L Q N R K |
| No.17 | D V P P P A V A ★ D S L V F T (W) P G V T E E S L V E K |
| No.18 | D P S L T L I A T S D T D P I F H E A V V W Y P P T E(E) V F F V Q N A G A P A A G T G L ★ K |
| No.19 | G N I I F A G E G Q G D D V P S A L Y L M N P L P(P) Y ★ T T T L X ---- |

★ : N residne glycosylated    X : Uncertain residne

FIG. 1

```
         10          20          30          40          50
AKLPSTAQII DQKSFNVLKP VPPPAVANDS LVFTWPGVTE ESLVEKPFHV
  No.8         No.9       No.17                        No.15
         60          70          80          90         100
YDEEFYDVIG KPPSLTLIAT SDTDPIFHEA VVWYPPTEEV FFVQNAGAPA
                         No.18
        110         120         130         140         150
AGTGLNKSSI IQKISLKEAD AVRKGKQDEV KVTVVDSNPQ VINPNGGTYY
  No.5       No.6  No.2                No.1
        160         170         180         190         200
KGNIIFAGEG QGDDVPSALY LMNPLPPYNT TTLLNNYFGR QFNSLNDVGI
  No.19
        210         220         230         240         250
NPRNGDLYFT DTLYGYLQDF RPVPGLRNQV YRYNFDTGAV TVVADDFTLP
        260         270         280         290         300
NGIGFGPDGK KVYVTDIGIA LGFYGRNLSS PASVYSFDVN QDGTLQNRKT
                No.16
        310         320         330         340         350
FAYVASFIPD GVHTDSKGRV YAGCGDGVHV WNPSGKLIGK IYTGTVAANF
  No.14              No.11                       No.3      No.12
        360         370         380
QFAGKGRMII TGQTKLFYVT LGASGPKLYD
  No.7             No.13                 No.4
```

FIG. 2

Sense primer (N-terminal sequence)

```
        Phe His Val Tyr Asp Glu Glu Phe Tyr Asp
5' AAAGC TTC CAC GTC TAC GAC GAA GAA TTC TAC GAC GT 3'
    HindIII  T       T   T   G   T   G   T   T   T
```

Antisense primer (Internal sequence)

```
          Pro Asn Trp Val His Val Gly Asp
5' GGCTTGCTGCA GGG GTT CCA AAC GTG AAC ACC GTC 3'
     PstI      A       C   A   C   C   A
                       G       G   G
                       T       T   T
```

FIG. 3

FL-E1 (Sense primer)

SD       MetAlaLysLeuProSerThrAlaGln
5' GTGAATTCTAAGGAGGAATAGGTGATGGCTAAGCTTCCTTCTACGGCTCAG 3'
  EcoRI       Stop Start FL-E2 (Antisense primer)

5' GTAAGTCTAGAGAAGTGAACATTTCTAATCATAGAG 3'
   XbaI

FIG. 4

```
         10        20        30        40        50        60
CCATGGTGGCTGCTAAGCTTCCTTCTACGGCTCAGATTATTGATCAGAAGTCGTTCAATG
        A  K  L  P  S  T  A  Q  I  I  D  Q  K  S  F  N  V
         70        80        90       100       110       120
TCTTGAAGGATGTGCCACCTCCTGCAGTGGCCAATGACTCTCTGGTGTTCACTTGGCCTG
  L  K  D  V  P  P  P  A  V  A  N  D  S  L  V  F  T  W  P  G
        130       140       150       160       170       180
GTGTAACTGAGGAGTCTCTTGTTGAGAAGCCTTTCCATGTCTACGATGAAGAGTTTTACG
   V  T  E  S  L  V  E  K  P  F  H  V  Y  D  E  E  F  Y  D
        190       200       210       220       230       240
ATGTAATTGGAAAAGACCCCTCTTTGACCCTCATCGCAACATCGGACACCGACCCAATCT
    V  I  G  K  D  P  S  L  T  L  I  A  T  S  D  T  D  P  I  F
        250       260       270       280       290       300
TCCATGAGGCTGTCGTATGGTATCCTCCTACTGAAGAGGTGTTCTTTGTGCAGAATGCTG
   H  E  A  V  V  W  Y  P  P  T  E  E  V  F  F  V  Q  N  A  G
        310       320       330       340       350       360
GCGCTCCTGCCGCAGGCACTGGCTTGAACAAGTCTTCCATCATTCAGAAGATTTCCCTCA
   A  P  A  A  G  T  G  L  N  K  S  S  I  I  Q  K  I  S  L  K
        370       380       390       400       410       420
AGGAGGCCGATGCTGTTCGCAAGGGCAAGCAGGATGAGGTCAAGGTCACAGTTGTTGACT
   E  A  D  A  V  R  K  G  K  Q  D  E  V  K  V  T  V  V  D  S
        430       440       450       460       470       480
CGAACCCTCAGGTTATCAACCCAAATGGTGGTACTTACTACAAGGGCAACATCATCTTCG
   N  P  Q  V  I  N  P  N  G  G  T  Y  Y  K  G  N  I  I  F  A
        490       500       510       520       530       540
CTGGTGAGGGCCAAGGCGACGATGTTCCCTCTGCGCTGTACCTCATGAACCCTCTCCCTC
   G  E  G  Q  G  D  D  V  P  S  A  L  Y  L  M  N  P  L  P  P
        550       560       570       580       590       600
CTTACAACACCACCACCCTTCTCAACAACTACTTCGGTCGCCAGTTCAACTCCCTCAACG
   Y  N  T  T  T  L  L  N  N  Y  F  G  R  Q  F  N  S  L  N  D
        610       620       630       640       650       660
ACGTCGGTATCAACCCCAGGAACGGTGACCTGTACTTCACCGATACCCTCTACGGATATC
   V  G  I  N  P  R  N  G  D  L  Y  F  T  D  T  L  Y  G  Y  L
        670       680       690       700       710       720
TCCAAGACTTCCGTCCTGTTCCTGGTCTGCGAAACCAGGTCTATCGTTACAACTTTGACA
   Q  D  F  R  P  V  P  G  L  R  N  Q  V  Y  R  Y  N  F  D  T
        730       740       750       760       770       780
CTGGCGCTGTCACTGTTGTCGCTGATGACTTTACCCTTCCCAACGGTATTGGCTTTGGCC
   G  A  V  T  V  V  A  D  D  F  T  L  P  N  G  I  G  F  G  P
        790       800       810       820       830       840
CCGACGGCAAGAAGGTTTATGTCACCGACACTGGCATCGCTCTCGGTTTCTACGGTCGCA
   D  G  K  K  V  Y  V  T  D  T  G  I  A  L  G  F  Y  G  R  N
        850       860       870       880       890       900
ACCTCTCTTCTCCCGCTTCTGTTTACTCTTTCGACGTGAACCAGGACGGTACTCTTCAGA
   L  S  S  P  A  S  V  Y  S  F  D  V  N  Q  D  G  T  L  Q  N
        910       920       930       940       950       960
ACCGCAAGACCTTTGCTTATGTTGCCTCATTCATCCCCGATGGTGTCCACACTGACTCCA
   R  K  T  F  A  Y  V  A  S  F  I  P  D  G  V  H  T  D  S  K
        970       980       990      1000      1010      1020
AGGGTCGTGTTTATGCTGGCTGCGGTGATGGTGTCCATGTCTGGAACCCCTCTGGCAAGC
   G  R  V  Y  A  G  C  G  D  G  V  H  V  W  N  P  S  G  K  L
       1030      1040      1050      1060      1070      1080
TCATCGGCAAGATCTACACCGGAACGGTTGCTGCTAACTTCCAGTTTGCTGGTAAGGGAA
   I  G  K  I  Y  T  G  T  V  A  A  N  F  Q  F  A  G  K  G  R
       1090      1100      1110      1120      1130      1140
GGATGATAATTACTGGACAGACCAAGTTGTTCTATGTCACTCTAGGGGCTTCGGGTCCCA
   M  I  I  T  G  Q  T  K  L  F  Y  V  T  L  G  A  S  G  P  K
       1150      1160      1170      1180      1190      1200
AGCTCTATGATTAGAAATGTTCACTTCTCTATACTTACATAGATAATACATGGCATTTGA
   L  Y  D  *
       1210      1220      1230
CTTTTGAAAAAAAAAAAAAAAAAACCATGG
```

FIG. 5

D-PANTOLACTONE HYDROLASE AND GENE ENCODING THE SAME

This application is a divisional of Ser. No. 08/836,047 filed on Sep. 19, 1997, now issued as U.S. Pat. No. 6,406,898, which is a 371 of PCT/JP96/02620 filed on Sep. 13, 1996, which claims priority to JAPAN 7-259451.

TECHNICAL FIELD

The present invention relates to a novel enzyme which is useful for an optical resolution of D,L-pantolactone through a D-selective asymmetric hydrolysis process and also to a gene encoding the same. More particularly, the present invention relates to proteins having a natural D-pantolactone hydrolase activity, produced by Fusarium oxysporum, or an activity substantially equivalent to the same and genes coding for the same. Specifically, the present invention relates to DNA containing a nucleotide sequence coding for said protein; to host cells transformed or transfected with said DNA; to a process for the production of said D-pantolactone hydrolase protein via using said host cells; and to the use of such proteins and host cells.

BACKGROUND ART

D-Pantolactone has been known as an intermediate in the preparation of D-pantothenic acid and pantethine which are useful as vitamins of medical or physiological importance. D-Pantolactone has heretofore been prepared through an optical resolution of a chemically-synthesized D,L-pantolactone. Such a process, however, has disadvantages in that it requires the use of expensive optical resolving agents such as quinine or brucine and further that the recovery of D-pantolactone is not easy. In order to solve such problems, the present inventors already proposed an optical resolving method by an enzymatic asymmetric hydrolysis of D,L-pantolactone in Unexamined Japanese Patent Publication (KOKAI TOKKYO) Nos. Hei 03-65,198 and Hei 04-144,681.

Thus, it is a process for the production of D-pantolactone, wherein the D-pantolactone in D,L-pantolactone mixtures is selectively subjected to an asymmetric hydrolysis using a microorganism possessing a lactone-hydrolyzing activity to form D-pantoic acid, which is then separated and converted into D-pantolactone, wherein said microorganism is a member selected from the group consisting of microorganisms belonging to the genera: Fusarium, Cylindrocarpon, Gibberella, Aspergillus, Penicillium, Rhizopus, Volutella, Gliocladium, Eurotium, Nectoria, Schizophyllum, Myrothecium, Neurospora, Acremonium, Tuberculina, Absidia, Sporothrix, Verticillium and Arthroderma. It is also a process for producing D-pantolactone hydrolase which comprises using a microorganism belonging to the above-mentioned genus.

However, it cannot be always said that many of those microorganisms disclosed as above possess a hydrolyzing activity to such an extent that they are immediately applicable in industry. Furthermore, in increasing the enzymatic activity of said microorganisms to an industrially applicable level, troublesome and difficult investigations requiring long time are needed for establishing conditions for growth of cells, conditions for enzyme activity induction, etc. There is another problem that, since said microorganisms are true fungus, their cell bodies are in variously shaped hyphae and, as compared with bacteria having a single shape, it is considerably difficult to prepare immobilized cells which are advantageous for industrial production. There is still another problem that, in purifying the enzyme from the cells, its recovery rate is considerably poor so far as D-pantolactone hydrolase is concerned.

DISCLOSURE OF THE INVENTION

An object of the present invention is to solve those problems and also to provide means for making a significant increase of the enzymatic activity possible, for example, means for modifying and improving the D-pantolactone hydrolase per se.

Thus, one aspect of the present invention is to disclose and provide a novel gene which codes for a protein having either a naturally-occurring D-pantolactone hydrolase activity (such as a Fusarium oxysporum D-pantolactone hydrolase activity) or an activity substantially equivalent thereto; a host cell transformed with DNA containing a nucleotide sequence coding for said protein; a process for producing said protein via using said host cell; and uses of said proteins and host cells.

The present invention directed to a gene coding for D-pantolactone hydrolase isolated from the above-mentioned microorganisms possessing the ability to hydrolyze a lactone and a system, with a high efficiency and rich productivity, for producing D-pantolactone is successfully developed through utilizing the D-pantolactone hydrolase gene isolated as such, not only solves the above-mentioned various problems but also greatly contributes to the development of enzymes possessing the ability to hydrolyze a lactone, together with new functions; and to the development of techniques using the novel enzyme. Particularly, the present inventors have succeeded in isolating a novel gene coding for a hydrolase with a D-pantolactone hydrolyzing ability, derived from microorganisms of the genus Fusarium (such as Fusarium oxysporum) which produces the D-pantolactone hydrolase, whereby the present invention has been achieved.

The present invention relates to:
(i) a protein having a natural D-pantolactone hydrolase activity or an activity substantially equivalent thereto or a salt thereof; or
(ii) a protein having a primary structural conformation substantially equivalent thereto or a salt thereof;
(iii) a characteristic partial peptide of said protein or a salt thereof;
(iv) genes, such as DNA and RNA, coding for said protein;
(v) vectors or plasmids, containing said gene operably in a gene recombination technique;
(vi) host cells transformed with such a vector, etc.;
(vii) a process for producing said protein or a salt thereof which comprises culturing said host cell;
(viii) a process for producing D-pantolactone which comprises an optical resolution of D,L-pantolactone with such a gene-manipulated host cell (transformant), such a recombinant protein or a salt thereof, etc.; and
(ix) a system means, such as an immobilized enzyme, for producing D-pantolactone.

In the present invention, a preferred recombinant protein is a D-pantolactone hydrolase having an amino acid sequence of SEQ ID NO:1 or an amino acid sequence substantially equivalent thereto, or a salt thereof.

Accordingly, one aspect of the present invention is:
(1) a protein having a naturally-occurring D-pantolactone hydrolase activity or an activity substantially equivalent thereto or having a primary structural conformation substantially equivalent thereto, or a salt thereof;

(2) the protein according to the above (1), wherein said protein having a naturally-occurring D-pantolactone hydrolase activity is originating in a microorganism belonging to a member selected from the group consisting of genera: Fusarium, Cylindrocarpon, Gibberella, Aspergillus, Penicillium, Rhizopus, Volutella, Gliocladium, Eurotium, Nectoria, Schizophyllum, Myrothecium, Neurospora, Acremonium, Tuberculina, Absidia, Sporothrix, Verticillium and Arthroderma;

(3) the protein according to the above (1), wherein said protein having a naturally-occurring D-pantolactone hydrolase activity is originating in the genus Fusarium;

(4) the protein according to any of the above (1) to (3), which is a D-pantolactone hydrolase, or a salt thereof, having an amino acid sequence represented by SEQ ID NO:1 or an amino acid sequence substantially equivalent thereto;

(5) the protein according to any of the above (1) to (4), which is produced by expressing an exogenous DNA sequence in procaryotic host cells;

(6) the protein according to any of the above (1) to (5), which has an amino acid sequence represented by SEQ ID NO:1 or the substantially same amino acid sequence as it has;

(7) a partial peptide, or a salt thereof, of the protein according to any of the above (1) to (6);

(8) a nucleic acid having a nucleotide sequence coding for the protein or partial peptide thereof according to any of the above (1) to (7);

(9) the nucleic acid according to the above (8), which has a nucleotide sequence having a portion corresponding to an open reading frame in the nucleotide sequence of SEQ ID NO:2 or a nucleotide sequence having an activity substantially equivalent thereto;

(10) a vector carrying the nucleic acid according to the above (8) or (9);

(11) a transformant wherein the vector according to the above (10) is harbored;

(12) a process for producing the protein or partial peptide thereof according to any of the above (1) to (7), including a D-pantolactone hydrolase or a salt thereof, which comprises:

culturing the transformant according to the above (11) in a nutrient medium suitable for growing said transformant to produce, as a recombinant protein, the protein or partial peptide thereof according to any of the above (1) to (7), including said D-pantolactone hydrolase or a salt thereof; and

(13) a process for producing D-pantolactone, which comprises:

carrying out an optical resolution of D,L-pantolactone in the presence of
(i) the protein or partial peptide thereof according to any of the above (1) to (7) or
(ii) the transformant according to the above (11).

More specifically, the present invention provides a D-pantolactone hydrolase, or a salt thereof, having an amino acid sequence of SEQ ID NO:1.

BRIEF DESCRIPTION OF DRAWINGS

FIG. 1 shows the amino acid sequences (residues 1–30 of SEQ ID NO: 1, residues 127–131 of SEQ ID NO: 1, residues 118–124 of SEQ ID NO: 1, residues 337–340 of SEQ ID NO: 1, residues 378–380 of SEQ ID NO: 1, residues 108–113 of SEQ ID NO: 1, residues 114–117 of SEQ ID NO: 1, SEQ ID NO: 3, residues 3–13 of SEQ ID NO: 1, residues 14–19 of SEQ ID NO: 1, residues 132–151 of SEQ ID NO: 1, SEQ ID NO: 4, residues 341–355 of SEQ ID NO: 1, residues 366–377 of SEQ ID NO: 1, residues 300–317 of SEQ ID NO: 1, residues 47–61 of SEQ ID NO: 1, residues 262–299 of SEQ ID NO: 1, residues 20–46 of SEQ ID NO: 1, residues 62–107 of SEQ ID NO: 1, SEQ ID NO: 5) obtained by sequencing of digestive peptides of D-pantolactone hydrolase.

FIG. 2 shows sites each corresponding to a digestive peptide of D-pantolactone hydrolase on the amino acid sequence (SEQ ID No: 1) for when the isolated cDNA codes.

FIG. 3 shows the structures of primers (SEQ ID NOS. 7 & 9) applied in PCR wherein a genomic DNA for D-pantolactone hydrolase is used as a template (SEQ ID NCS. 6 & 8).

FIG. 4 shows the structures of primers (SEQ ID NOS 10 & 12) applied in PCR for the construction of a vector used for expressing recombinant D-pantolactone hydrolase (SEQ ID NO: 11).

FIG. 5 shows the amino acid sequence (SEQ ID NO: 1) and nucleotide sequence (SEQ ID ND: 2) of D-pantolactone hydrolase.

DETAILED DESCRIPTION OF THE INVENTION

The present invention provides techniques such as cloning of a gene coding for naturally-occurring D-pantolactone hydrolase (such as natural D-pantolactone hydrolase derived from (or originating in) *Fusarium oxysporum*) or a protein having an activity substantially equivalent thereto, identification of said gene and determination of the characteristic sequence (sequencing) of said gene as well as recombination of said gene to an expression vector; production and culture/growth of host cells transformed with DNA containing a nucleotide sequence coding for said protein (transformants); production of said protein via using said host cell; and use of such proteins and host cells.

Described herein below are detailed techniques and operations according to the present invention.

The present invention also provides various means for utilizing genes coding for the above-mentioned D-pantolactone hydrolase and further provides a D-pantolactone hydrolase production system with a good efficiency and a more excellent productivity wherein said isolated D-pantolactone hydrolase gene is utilized.

The present invention relates to a protein having a naturally-occurring D-pantolactone hydrolase activity or an activity substantially equivalent thereto or a salt thereof, or a protein having a primary structural conformation substantially equivalent thereto or a salt thereof; a characteristic partial peptide of said protein or a salt thereof; a gene, such as DNA and RNA, coding for said protein or peptide; a vector or plasmid (or vehicle) containing said gene operably in a gene recombination technique; a host cell transformed with such a vector, etc.; a process for producing said protein or a salt thereof which comprises culturing said host cell; a process for synthesizing D-pantolactone which comprises an optical resolution of D,L-pantolactone with such a gene-manipulated host cell, or said recombinant protein or a salt thereof; and systems and means, such as immobilized enzymes, for producing D-pantolactone.

In the present invention, D-pantolactone hydrolase or a salt thereof which comprises, preferably, an amino acid sequence of SEQ ID NO:1 or a amino acid sequence substantially equivalent thereto is specifically illustrated but the D-pantolactone hydrolase of the present invention includes any enzyme which has a D-pantolactone hydrolyzing ability as long as it has a novel amino acid sequence. The D-pantolactone hydrolyzing ability refers to any ability which is in the same quality in view of hydrolyzing D-pantolactone. More preferably, the D-pantolactone hydrolase of the present invention includes all substances having an amino acid sequence of SEQ ID NO:1; or having a substantially equivalent amino acid sequence thereto and/or the substantially same amino acid sequence.

The D-pantolactone hydrolase gene according to the present invention may be cloned, for example, by the following processes:

It should be noted that gene recombination techniques may be conducted, for example, by the methods disclosed in T. Maniatis et al., "Molecular Cloning", 2nd Ed., Cold Spring Harbor Laboratory, Cold Spring Harbor, N. T. (1989); Nippon Seikagaku Kai (Biochemical Society of Japan) ed., "Zoku-Seikagaku Jikken Kouza 1, Idensi Kenkyuho II (Lectures on Biochemical Experiments (Second Series; 1), Methods for Gene Study II)", Tokyo Kagaku Dojin, Japan (1986); Nippon Seikagaku Kai (Biochemical Society of Japan) ed., "Shin-Seikagaku Jikken Kouza 2, Kakusan III (Kumikae DNA Gijutsu) (New Lectures on Biochemical Experiments 2, Nucleic Acids III (Recombinat DNA Technique))", Tokyo Kagaku Dojin, Japan (1992); R. Wu (ed.), "Methods in Enzymology", Vol. 68, Academic Press, New York (1980); R. Wu et al. (ed.), "Methods in Enzymology", Vols. 100 and 101, Academic Press, New York (1983); R. Wu et al. (ed.), "Methods in Enzymology", Vols. 153, 154 and 155, Academic Press, New York (1987), etc. as well as by the techniques disclosed in the references cited therein, the disclosures of which are hereby incorporated by reference, or by the substantially same techniques as they disclose or modified techniques thereof. Such techniques and means may also be those which are individually modified/improved from conventional techniques depending upon the object of the present invention.

1) Cloning of Partial Genomic DNA of D-Pantolactone Hydrolase

Cultured *Fusarium oxysporum* cells are disrupted, and centrifuged to isolate chromosomal DNA, followed by decomposition and removal of RNA, in a conventional manner. DNA components are purified by removing proteins therefrom. Further information on preparation of the materials referred to in this application is disclosed, for example, in "Shokubutsu Biotechnology-Jikken Manual (Plant Biotechnology Experiment Manual)", Noson Bunkasha, page 252, the disclosures of which are hereby incorporated by reference.

As a source for DNA, any microorganism which belongs to the genus Fusarium and has an ability of producing D-pantolactone hydrolase may be suitably used. Examples of the microorganism belonging to the genus Fusarium which is applicable here are *Fusarium oxysporum* IFO 5942, *Fusarium semitectam* IFO 30200, etc.

Similarly, other microorganisms which belong to a member selected from the group consisting of the genera: Cylindrocarpon, Gibberella, Aspergillus, Penicillium, Rhizopus, Volutella, Gliocladium, Eurotium, Nectoria, Schizophyllum, Myrothecium, Neurospora, Acremonium, Tuberculina, Absidia, Sporothrix, Verticillium or Arthroderma and have the ability to produce D-pantolactone hydrolase may be used as a source for DNA. Examples of such microorganisms are *Cylindrocarpon tonkinense* IFO 30561, *Gibberella fujikuroi* IFO 6349, *Aspergillus awamori* IFO 4033, *Penicillium chrysogenum* IFO 4626, *Rhizopus oryzae* IFO 4706, *Volutella buxi* IFO 6003, *Gliocladium catenulatum* IFO 6121, *Eurotium chevalieri* IFO 4334, *Nectria elegans* IFO 7187, *Schizophyllum commune* IFO 4928, *Myrothecium roridum* IFO 9531, *Neurospora crassa* IFO 6067, *Acremonium fusidioides* IFO 6813, *Tuberculina persicina* IFO 6464, *Absidia lichtheimi* IFO 4009, *Sporothrix schenckii* IFO 5983, *Verticillium malthousei* IFO 6624, *Arthroderma uncinatum* IFO 7865, etc., wherein "IFO" is Zaidan-Hojin Hakko Kenkyusho (the Institute for Fermentation, Osaka; 17–85, Juso-hon-machi 2-chome, Yodogawa-ku, Osaka 532, Japan) and each number thereafter stands for the number in the Catalog issued by said IFO or the Accession Number given by IFO.

2) Preparation of Probe

Synthetic oligonucleotide primers are prepared according to information on amino acid sequences regarding the internal peptide of D-pantolactone hydrolase. For example, synthetic oligonucleotide primers can be prepared according to information on amino acid sequences regarding the internal peptide of pure D-pantolactone hydrolase obtained from the microorganism which is selected from those mentioned hereinabove and has an ability of producing D-pantolactone hydrolase. In a typical case, degenerate primers, etc. are designed and prepared based upon information on the amino acid sequence of natural D-pantolactone hydrolase fragments. Preparation of primers may be carried out by techniques which are known in the art. For example, the primers may be synthesized by means of a phosphodiester method, a phosphotriester method, a phosphoamidite method, etc. using an automatic DNA synthesizer. To be more specific, D-pantolactone hydrolase is purified from the cells obtained by culturing *Fusarium oxysporum* IFO 5942 in a nutrient medium and fragmented, if necessary, with a peptidase, etc. whereupon the information on an amino acid sequence of the internal peptide of the enzyme is collected. From the information on the amino acid sequence obtained as such, preferred synthetic oligonucleotide primers are designed and prepared. A polymerase chain reaction (PCR) is carried out using a pair of said primers wherein a genomic DNA for D-pantolactone hydrolase is used as a template. The PCR may be carried out by techniques known in the art or by methods substantially equivalent thereto or modified techniques. The reaction may be conducted by the methods disclosed, for example, in R. Saiki, et al., Science, Vol. 230, pp. 1350 (1985); R. Saiki, et al., Science, Vol. 239, pp. 487 (1988); and Henry A. Erlich, PCR Technology, Stockton Press. The reaction may also be carried out, for example, using a commercially available kit or reagent.

The resulting amplified DNA fragments are sequenced and, after confirming that they contain a sequence which is homologous to that coding for the amino acid sequence of the internal peptide of the purified enzyme, they are labeled with an isotope and are used for future experiments or the like. Sequencing of nucleotide sequences may be carried out by a dideoxy technique (such as an M13 dideoxy method), a Maxam-Gilbert method, etc. or may be carried out using a commercially available sequencing kit such as a Taq dyeprimer cycle sequencing kit or an automatic nucleotide sequencer such as a fluorescent DNA sequencer. Labeling of probes, etc. with a radioisotope, etc., may be carried out using a commercially available labeling kit such as a random primed DNA labeling kit (Boehringer Mannheim).

3) Cloning of D-Pantolactone Hydrolase cDNA a) Preparation of mRNA and Construction of cDNA Library.

Cultured *Fusarium oxysporum* cells are disrupted, extracted according to an AGPC method to isolate total RNA. Then mRNA is isolated and purified from the total RNA fraction by a suitable method such as by the use of an oligo dT cellulose column. Although, in an embodiment, mRNA may be isolated with a method known in the art or by the substantially same method as it is or modifications thereof, the isolation and purification of mRNA can be conducted by methods disclosed in, for example, T. Maniatis, et al., "Molecular Cloning", 2nd Ed., Chapter 7, Cold Spring Harbor Laboratory, Cold Spring Harbor, N. T. (1989); L. Grossman, et al. ed., "Methods in Enzymology", Vol. 12, Parts A & B, Academic Press, New York (1968); S. L. Berger et al. ed., "Methods in Enzymology", Vol. 152, p. 33 & p. 215, Academic Press, New York (1987); Biochemistry, 18, 5294–5299, 1979; etc., the disclosures of which are hereby incorporated by reference. Examples of such mRNA isolating and purifying techniques are a guanidine-cesium chloride method, a guanidine thiocyanate method, a phenol method, etc. If necessary, the resulting total RNA may be subjected to a purification process using an oligo(dT)-cellulose column, etc. to give poly(A)$^+$mRNA. As a source for mRNA, any microorganism which belongs to the genus Fusarium and has an ability of producing D-pantolactone hydrolase may be suitably used. Examples of the microorganism belonging to the genus Fusarium which is applicable herein are *Fusarium oxysporum* IFO 5942, *Fusarium semitectam* IFO 30200, etc. Similarly, other microorganisms which belong to a member selected from the group consisting of the genera: Cylindrocarpon, Gibberella, Aspergillus, Penicillium, Rhizopus, Volutella, Gliocladium, Eurotium, Nectoria, Schizophyllum, Myrothecium, Neurospora, Acremonium, Tuberculina, Absidia, Sporothrix, Verticillium or Arthroderma and have an ability of producing D-pantolactone hydrolase may be used as a source for mRNA. Examples of such microorganisms are *Cylindrocarpon tonkinense* IFO 30561, *Gibberella fujikuroi* IFO 6349, *Aspergillus awamori* IFO 4033, *Penicillium chrysogenum* IFO 4626, *Rhizopus oryzae* IFO 4706, *Volutella buxi* IFO 6003, *Gliocladium catenulatum* IFO 6121, *Eurotium chevalieri* IFO 4334, *Nectria elegans* IFO 7187, *Schizophyllum commune* IFO 4928, *Myrothecium roridum* IFO 9531, *Neurospora crassa* IFO 6067, *Acremonium fusidioides* IFO 6813, *Tuberculina persicina* IFO 6464, *Absidia lichtheimi* IFO 4009, *Sporothrix schenckii* IFO 5983, *Verticillium malthousei* IFO 6624, *Arthroderma uncinatum* IFO 7865, etc.

cDNAs are prepared by using, as a template, the resulting mRNA and a reverse transcriptase, etc. The reverse transcriptase synthesis of cDNA using mRNA may be carried out by standard techniques known in the art, by the substantially same techniques or by modified techniques thereof. Detailed techniques are found in, for example, H. Land et al., "Nucleic Acids Res.", Vol. 9, 2251 (1981); U. Gubler et al., "Gene", Vol. 25, 263–269 (1983); S. L. Berger et al. ed., "Methods in Enzymology", Vol. 152, p. 307, Academic Press, New York (1987); etc., the disclosures of which are hereby incorporated by reference. The cDNA thus obtained is inserted into a commercially available phage vector or, further, subjected to a packaging by conventional techniques. Then, based upon the cDNA thus prepared, cDNA libraries can be constructed.

b) Cloning of D-Pantolactone Hydrolase cDNA.

The above recombinant phage was transfected into host cells, followed by subjecting to a plaque hybridization to select positive plaques (clones). DNA fragments from the resulting clones are sequenced. The resultant nucleotide sequences are decoded and analyzed in view of an encoded amino acid sequence. As a result of such analyses and investigations, it is confirmed that the target D-pantolactone hydrolase gene is cloned.

Besides the technique using a phage vector, transformations of host cells including *Escherichia coli* may be conducted according to techniques known in the art, such as a calcium technique and a rubidium/calcium technique, or the substantially same methods (D. Hanahan, J. Mol. Biol., Vol. 166, p. 557 (1983), etc.).

PCR may be conducted using the prepared cDNA as a template. In an embodiment, the primer obtained in the above 2) can be used.

With respect to a plasmid into which the D-pantolactone hydrolase gene is incorporated, any plasmid may be used as long as said DNA can be expressed in host cells conventionally used in gene engineering techniques (such as procaryotic host cells including *Escherichia coli, Bacillus subtilis*, etc. and eucaryotic host cells including yeasts). In such a sequence of the plasmid, it is possible, for example, to incorporate codons suitable for expressing the cloned DNA in selected host cells or to construct restriction enzyme sites. It is also possible to contain control sequences, promotion sequences, etc. for facilitating the expression of the aimed gene; linkers, adaptors, etc. useful for ligating the aimed gene; sequences useful in controlling resistance to antibiotics or in controlling metabolism or in selection; and the like.

Preferably, suitable promoters may be used. For example, such promoters may include tryptophan (trp) promoter, lactose (lac) promoter, tryptophan-lactose (tac) promoter, lipoprotein (lpp) promoter, λ phage $P_L$ promoter, etc. in the case of plasmids where *Escherichia coli* is used as a host; and GAL1, GAL10 promoters, etc. in the case of plasmids where yeast is used as a host.

Examples of the plasmid suitable for host *Escherichia coli* are pBR322, pUC18, pUC19, pUC118, pUC119, pSP64, pSP65, pTZ-18R/-18U, pTZ-19R/-19U, pGEM-3, pGEM-4, pGEM-3Z, pGEM-4Z, pGEM-5Zf(−), pBluescript KS™ (Stratagene), etc. Examples of the plasmid vector suitable for expression in *Escherichia coli* are pAS, pKK223 (Pharmacia), pMC1403, pMC931, pKC30, etc. Examples of the plasmid for host yeasts are YIp vector, YEp vector, YRp vector, YCp vector, etc., including pGPD-2, etc. *Escherichia coli* host cells may include those derived from *Escherichia coli* K12 strains, such as NM533, XL1-Blue, C600, DH1, HB101 and JM109.

In the gene engineering techniques of the present invention, it is possible to use various restriction enzymes, reverse transcriptases, enzymes for DNA modification and decomposition, used for modifying or converting a DNA fragment to a structure suitable for cloning, DNA polymerases, terminal nucleotidyl transferases, DNA ligases; etc., which are known or common in the art. Examples of the restriction enzyme are those disclosed in R. J. Roberts, "Nucleic Acids Res.", Vol. 13, r165 (1985); S. Linn et al. ed., "Nucleases", p. 109, Cold Spring Harbor Lab., Cold Spring Harbor, N.Y., 1982; etc. Examples of the reverse transferase are those derived from mouse Moloney leukemia virus (MMLV), from avian myeloblastosis virus (AMV), etc. Particularly, RNase H-deficient reverse transferase or the like is preferably used. Examples of the DNA polymerase are *Escherichia coli* DNA polymerase, Klenow fragment which is a derivative of *E. coli* DNA polymerase, *E. coli* phage T4 DNA polymerase, *E. coli* phage T7 DNA polymerase, thermoduric bacteria DNA polymerase, etc.

The terminal nucleotidyl transferase includes TdTase capable of adding a dideoxynucleotide (dNMP) to a 3'-OH terminal, as disclosed in R. Wu et al. ed., "Methods in Enzymology", Vol. 100, p. 96, Academic Press, New York (1983). The enzyme for modifying and decomposing DNA includes exonuclease, endonuclease, etc. Examples of such enzymes are snake toxin phosphodiesterase, spleen phosphodiesterase, E. coli DNA exonuclease I, E. coli DNA exonuclease III, E. coli DNA exonuclease VII, λ exonuclease, DNase I, nuclease S1, Micrococcus nuclease, etc. Examples of the DNA ligase are E. coli DNA ligase, T4 DNA ligase, etc.

The vector (or vehicle) which is suitable for cloning DNA genes and constructing DNA libraries includes plasmid, λ phage, cosmid, P1 phage, F factor, YAC, etc. Preferred examples of such vectors are vectors derived from λ phage, such as Charon 4A, Charon 21A, λ gt10, λ gt11, λ DASHII, λ FIXII, λ EMBL3 and λ ZAPII™ (Stratagene), etc.

In addition, based upon the gene nucleotide sequence encoding the D-pantolactone hydrolase of the present invention, methods and means conventionally used in gene engineering techniques enable us to manufacture proteins, such as variants and mutants, wherein a modification is introduced into the amino acid sequence of the D-pantolactone hydrolase in such a manner that one or more amino acid(s) is/are substituted, deleted, inserted, translocated or added. Examples of the methods and means for such a variation, substitution and modification are those disclosed in Nippon Seikagaku Kai (Biochemical Society of Japan) ed., "Zoku-Seikagaku Jikken Kouza 1, Idensi Kenkyuho II (Lectures on Biochemical Experiments (Second Series; 1), Methods for Gene Study II)", p.105 (Susumu Hirose), Tokyo Kagaku Dojin, Japan (1986); Nippon Seikagaku Kai (Biochemical Society of Japan) ed., "Shin-Seikagaku Jikken Kouza 2, Kakusan III (Kumikae DNA Gijutsu) (New Lectures on Biochemical Experiments 2, Nucleic Acids III (Recombinat DNA Technique))", p. 233 (Susumu Hirose), Tokyo Kagaku Dojin, Japan (1992); R. Wu, L. Grossman, ed., "Methods in Enzymology", Vol. 154, p. 350 and p. 367, Academic Press, New York (1987); R. Wu, L. Grossman, ed., "Methods in Enzymology", Vol. 100, p.457 and p. 468, Academic Press, New York (1983); J. A. Wells et al., "Gene", Vol. 34, p. 315 (1985); T. Grundstroem et al., "Nucleic Acids Res.", Vol. 13, p. 3305 (1985); J. Taylor et al., "Nucleic Acids Res.", Vol. 13, p. 8765 (1985); R. Wu, ed., "Methods in Enzymology", Vol. 155, p. 568, Academic Press, New York (1987); A. R. Oliphant et al., "Gene", Vol. 44, p.177 (1986); etc., the disclosures of which are hereby incorporated by reference. Examples of such methods and means are techniques utilizing synthetic oligonucleotides for introducing a mutation or variation into a specific site (site-directed mutagenesis techniques), Kunkel techniques, dNTP[α S] techniques (Eckstein method), techniques using sulfurous acid (or bisulfite), nitrous acid (or nitrite), etc. for introducing a mutation or variation into a specific domain or area, etc.

Moreover, the resulting protein according to the present invention may be subjected to chemical techniques whereby an amino acid residue(s) contained therein is(are) modified or may be made into its(their) derivative(s) by subjecting to a partial decomposition or a modification using an enzyme such as peptidase (for example, pepsin, chymotrypsin, papain, bromelain, endopeptidase, exopeptidase, etc.). It is also possible to express, as fusion proteins, the recombinant proteins of the present invention on the manufacture by means of gene recombinant techniques and then to convert/process the fusion proteins in vivo or in vitro to products having a biological activity substantially equivalent to a natural D-pantolactone hydrolase. A fusion production conventionally used in gene engineering techniques may be used as well. Such a fusion protein may be purified by means of an affinity chromatography, etc. utilizing its fusion part. Modifications, alterations, etc. of protein structures are found, for example, in Nippon Seikagaku Kai (Biochemical Society of Japan) ed., "Shin-Seikagaku Jikken Kouza 1, Tanpakushitsu VII, Tanpakushitsu Kogaku (New Lectures on Biochemical Experiments 1, Protein VII, Protein Engineering)", Tokyo Kagaku Dojin, Japan (1993), the disclosures of which are hereby incorporated by reference. Such modifications, alterations, etc. may be conducted according to techniques disclosed therein, techniques disclosed in references cited therein, and those substantially similar thereto.

Thus, the products according to the present invention may include either proteins wherein one or more amino acid residue(s) is/are different from that/those of the natural one in terms of identity or proteins wherein one or more amino acid residue(s) is/are shifted from the position(s) of the natural one. The products according to the present invention may include deletion analogs wherein one or more amino acid residue(s) specified for the natural D-pantolactone hydrolase is/are deficient therefrom (for example, 1 to 80, preferably 1 to 60, more preferably 1 to 40, still more preferably 1 to 20 and particularly preferably 1 to 10 amino acid residue(s) specified for the natural D-pantolactone hydrolase is/are deficient therefrom); substitution analogs, wherein one or more amino acid residue(s) specified for the natural D-pantolactone hydrolase is/are replaced with other residue(s) (for example 1 to 80, preferably 1 to 60, more preferably 1 to 40, still more preferably 1 to 20 and particularly preferably 1 to 10 amino acid residue(s) specified for the natural D-pantolactone hydrolase is/are replaced with other residue(s)); and addition analogs, wherein one or more amino acid residue(s) is/are added to the sequence specified for the natural D-pantolactone hydrolase (for example 1 to 80, preferably 1 to 60, more preferably 1 to 40, still more preferably 1 to 20 and particularly preferably 1 to 10 amino acid residue(s) is/are added to the amino acid sequence specified for the natural D-pantolactone hydrolase. The products may include proteins wherein a domain structure characteristic to the natural D-pantolactone hydrolase is contained or retained. Further, the products may include proteins having the same quality in view of D-pantolactone hydrolase activity as the natural D-pantolactone hydrolase.

The products of the present invention may include all of the variants and analogs as mentioned herein above, as long as they have the domain structure which is characteristic to the naturally-occurring D-pantolactone hydrolase. It is also believed that the products of the present invention may include all proteins having a primary structural conformation substantially equivalent to that of the naturally-occurring D-pantolactone hydrolase according to the present invention and those having a portion of the primary structural conformation of naturally-occurring D-pantolactone hydrolase according to the present invention. It is further believed that the products of the present invention may include proteins sharing all or part of the biological properties of naturally-occurring D-pantolactone hydrolase or having a biological activity substantially equivalent to that of the natural D-pantolactone hydrolase. Furthermore, the product of the present invention may include one of the variants which naturally occur. The D-pantolactone hydrolase products of the present invention can be separated, isolated or/and purified as illustrated hereinafter.

Further, the products according to the present invention may include DNA sequences coding for the above-mentioned polypeptide and DNA sequences encoding D-pantolactone hydrolase polypeptides (including analogs and derivatives thereof) having all or part of the natural characteristics of the naturally-occurring D-pantolactone hydrolase. Said D-pantolactone hydrolase nucleotide sequences may also be modified (such as inserted, added, deleted and substituted). Thus, the products according to the present invention may include such modified nucleotide sequences as well.

Since the DNA sequences of the present invention provide information on the amino acid sequence of D-pantolactone hydrolase protein which has heretofore been unavailable, utilization of such information is within the scope of the present invention as well. Such utilization may include designing of probes for isolation and/or detection of genomic DNA and cDNA coding for D-pantolactone hydrolase or proteins related thereto, of microorganisms, or particularly preferably microorganisms having an ability of producing D-pantolactone hydrolase, such as those belonging to a member selected from the group consisting of the genera: Fusarium, Cylindrocarpon, Gibberella, Aspergillus, Penicillium, Rhizopus, Volutella, Gliocladium, Eurotium, Nectoria, Schizophyllum, Myrothecium, Neurospora, Acremonium, Tuberculina, Absidia, Sporothrix, Verticillium and Arthroderma with an ability of producing D-pantolactone hydrolase.

The DNA sequences of the present invention are valuable, for example, as probes for isolation and/or detection of genomic DNA and cDNA coding for D-pantolactone hydrolase or proteins related thereto, of microorganisms having an ability of producing D-pantolactone hydrolase, or particularly preferably microorganisms belonging to the above-mentioned genus, including the Fusarium, etc. Isolation of the gene may be carried out by utilizing PCR techniques or RT-PCR techniques (PCR using a reverse transcriptase (RT)). D-Pantolactone hydrolase DNA and its related DNA may be utilized for isolation, detection, etc. of genes related to D-pantolactone hydrolase by means of PCR techniques, RT-PCR techniques or other methods, using a DNA primer obtained by a chemical synthesis as a result of selecting a characteristic domain (or portion) based upon a putative amino acid sequence derived from the cloned and sequenced D-pantolactone hydrolase cDNA sequence and of designing the DNA primer relied on the selected domain (or portion).

As mentioned hereinabove, the present invention provides a process for producing the aimed D-pantolactone hydrolase which comprises importing a recombinant D-pantolactone hydrolase DNA molecule and/or gene into hosts followed by expressing the D-pantolactone hydrolase therein. Thus, in accordance with the present invention, recombinants (transformants) or transfectants which are endowed with the capacity to substantially express the same; and use thereof are provided.

Another aspect of the present invention also relates to nucleic acids, such as DNA and RNA, which enable the expression in eucaryotic or procaryotic host cells, such as *Escherichia coli* host cells of (1) proteins or salts thereof having a D-pantolactone hydrolase activity;

(2) proteins or salts thereof characterized in having a substantially equivalent activity thereto; or (3) polypeptides having all or at least a part of a D-pantolactone hydrolase protein or a salt thereof (more preferably D-pantolactone hydrolase protein originating in *Fusarium oxysporum*) and having the substantially equivalent activity or the substantially same primary structural conformation.

In addition, such a nucleic acid, particularly DNA, may be:

(a) a sequence capable of encoding the amino acid sequence of SEQ ID NO:1 or a sequence complementary thereto;

(b) a sequence capable of hybridizing with said DNA sequence (a) or a fragment thereof; and (c) a sequence having a degenerate code capable of hybridizing with the sequence (a) or (b).

The characteristics of the present invention reside in eucaryotic or procaryotic host cells, such as *Escherichia coli* host cells, transformed or transfected with such a nucleic acid, which are endowed with the capacity to express said polypeptide of the present invention.

It may also be possible in accordance with the present invention to obtain a microorganism in which its ability to produce D-pantolactone hydrolase is modified by introducing (i) DNA coding for a protein having a D-pantolactone hydrolase activity or a protein having the substantially equivalent activity thereto or (ii) DNA, such as vector, containing said DNA into said microorganism in an expressible manner. Such microorganisms possessing the ability to produce D-pantolactone hydrolase may include microorganisms belonging to a member selected from the group consisting of the genera: Fusarium, Cylindrocarpon, Gibberella, Aspergillus, Penicillium, Rhizopus, Volutella, Gliocladium, Eurotium, Nectoria, Schizophyllum, Myrothecium, Neurospora, Acremonium, Tuberculina, Absidia, Sporothrix, Verticillium and Arthroderma. Examples of such microorganisms are *Fusarium oxysporum* IFO 5942, *Fusarium semitectam* IFO 30200, *Cylindrocarpon tonkinense* IFO 30561, *Gibberella fujikuroi* IFO 6349, *Aspergillus awamori* IFO 4033, *Penicillium chrysogenum* IFO 4626, *Rhizopus oryzae* IFO 4706, *Volutella buxi* IFO 6003, *Gliocladium catenulatum* IFO 6121, *Eurotium chevalieri* IFO 4334, *Nectria elegans* IFO 7187, *Schizophyllum commune* IFO 4928, *Myrothecium roridum* IFO 9531, *Neurospora crassa* IFO 6067, *Acremonium fusidioides* IFO 6813, *Tuberculina persicina* IFO 6464, *Absidia lichtheimi* IFO 4009, *Sporothrix schenckii* IFO 5983, *Verticillium malthousei* IFO 6624, *Arthroderma uncinatum* IFO 7865, etc.

Transformation may include techniques in which protoplast cells prepared by the use of a suitable cell wall lytic enzyme are contacted with DNA in the presence of calcium chloride, polyethylene glycol, etc.; electroporation techniques (see: for example, E. Neumann et al., EMBO J, Vol. 1, pp. 841 (1982), etc.); microinjection techniques; shot gun methods for shooting a gene with a gun; etc.

The enzymes can be isolated and prepared by purifying techniques from various materials, such as produced enzyme materials including cell growth culture medium, disrupted cultured cells, transformed cells, etc. The purification may include methods known in the art, including salting out such as precipitation with ammonium sulfate; gel filtration using Sephadex or the like; ion exchange chromatography technique using, for example, a carrier having a diethylaminoethyl group or a carboxymethyl group; hydrophobic chromatography technique using, for example, a carrier having hydrophobic groups including a butyl group, an octyl group, a phenyl group, etc.; pigment gel chromatography technique; electrophoresis technique; dialysis; ultrafiltration; affinity chromatography technique; high performance liquid chromatography technique; etc.

When the enzyme is obtained as an inclusion body, it may be subjected to a solubilizing treatment using, for example, a denaturing agent, such as guanidine hydrochloride and urea, and, if necessary, in the presence of a reducing agent, such as 2-mercaptoethanol and dithiothreitol, whereupon an activated form of the enzyme is produced.

For enzyme materials, enzyme-producing cells per se may be used instead. Immobilized enzymes may include products prepared by immobilizing the enzyme or enzyme-producing cells according to techniques known in the art. The immobilization can be conducted by carrier bonding techniques, such as a covalent method and an adsorption method, a cross-linking method, an encapsulation, etc. The immobilization can also be conducted using a condensing agent such as glutaraldehyde, hexamethylene diisocyanate and hexamethylene diisothiocyanate if necessary. In addition, monomer techniques in which monomers are gelled in a polymerization, prepolymer techniques in which molecules having bigger size than conventional monomers are polymerized, polymer techniques in which polymers are gelled, etc. may be exemplified. It may include an immobilization using polyacrylamide, an immobilization using natural polymers such as alginic acid, collagen, gelatin, agar and κ-carrageenan, an immobilization using synthetic polymers such as photosetting resins and urethane polymers, etc. It may be possible to carry out the optical resolution of lactone compounds by an enzymatic asymmetric hydrolysis utilizing a lactone hydrolase (such as a D-pantolactone hydrolysis using a culture of microorganisms and enzymes), as well as treatment of products obtained thereby in the same manner as disclosed in Unexamined Japanese Patent Publication (KOKAI TOKKYO) Nos. Hei 3-65,198 and Hei 4-144,681.

For example, the transformed microorganisms (transformants) thus obtained are subjected to shaking culture in a liquid medium. The resulting cultured cells are harvested, to which an aqueous solution of D,L-pantolactone (concentrations: 2 to 60%) is added. The mixture is made to react at 10 to 40° C. for from several hours to one day while adjusting the pH to from 6 to 8. After completion of the reaction, the cells are separated and the unreacted L-pantolactone in the reaction solution is separated by extracting with an organic solvent (preferably an ester such as ethyl acetate, an aromatic hydrocarbon such as benzene or a halogenated hydrocarbon such as chloroform). D-Pantoic acid remaining in the aqueous layer is heated under an acidic condition with hydrochloric acid to conduct a lactonation followed by extracting with the above-mentioned organic solvent whereupon the resulting D-pantolactone is obtained. As such, processed cells (dried cells, immobilized cells, etc.) of the transformed microorganisms or enzymes and immobilized enzymes obtained from the transformed cells can be used in the same manner as well.

As a result of utilization of various embodiments of the present invention as mentioned hereinabove, it is now possible to provide various technical means, such as means valuable or useful for the synthetic studies concerning an optical resolution of lactone compounds by an enzymatic asymmetric hydrolysis utilizing a lactone hydrolase (for example, D-pantolactone hydrolase) as well as means applicable to other uses. The present invention will be more specifically illustrated by way of the following examples although it is to be understood that the present invention is not limited to such examples but various embodiments within the spirit of this specification are possible.

Incidentally, when nucleotides (bases) and amino acids are indicated by abbreviations in the specification and in the drawings, they depend upon an "IUPAC-IUB Commission on Biochemical Nomenclature" or upon the meanings of the terms which are commonly used in the art. When optical isomers are present in amino acids, an L-isomer is referred to unless otherwise specified.

The transformant *Escherichia coli*, designated JM109 (EJM-ESE-1) having a recombinant vector (PFLC40E) into which the enzyme D-pantolactone hydrolase gene is integrated and obtained in Example 1 mentioned herein below has been deposited as from Aug. 30, 1995 (original deposit date) with the National Institute of Bioscience and Human Technology (NIBH), Agency of Industrial Science and Technology, Ministry of International Trade and Industry, Japan, located at 1-3, Higashi 1-chome, Tsukuba-shi, IBARAKI (Zip Code: 305), JAPAN and has been assigned the Accession Number FERM P-15141. The original deposit of the transformant *E. coli* JM109 (EJM-ESE-1) has been transferred to one under the Budapest Treaty by a request dated Aug. 28, 1996 and is on deposit with the Accession Number FERM BP-5638 under the terms of the Budapest Treaty at NIBH.

EXAMPLES

Described below are examples of the present invention which are provided only for illustrative purposes, and not to limit the scope of the present invention. In light of the present disclosure, numerous embodiments within the scope of the claims will be apparent to those of ordinary skill in the art.

Example 1

1) Amino Acid Sequencing of Purified Enzyme.

A sample of freeze-dried D-pantolactone hydrolase (14.3 nmol; subunit molecular weight: 60,000) prepared according to Example 1 in Unexamined Japanese Patent Publication (KOKAI TOKKYO) No. Hei 4-144,681 was dissolved in 44 $\mu$l of 50 mM Tris-HCl (pH: 9.0) containing 8M urea and was denatured at 37° C. for 1 hr. To this solution was added 44 $\mu$l of 50 mM Tris-HCl (pH: 9.0) whereupon the urea concentration was made 4M. Then 12 $\mu$l (0.144 nmol; E/S=1/100) of 12 nmol/ml of lysyl endopeptidase (Wako Pure Chemicals, Japan; was added thereto and a digestion was carried out at 30° C. for 12 hrs. The resulting digested peptide was collected by means of a reversed phase column (Nakara Tesuku, Japan) and analysis of the amino acid sequence was carried out using a 477A Protein Sequencer (ABI, USA).

| Collecting Conditions | |
| --- | --- |
| Column: | Cosmosil 5C18-AR (4.6 × 250 mm) |
| Flow Rate: | 1 ml/min. |
| Temperature: | 35° C. |
| Detecting Wave Length: | 210 nm |
| Eluting Solution: | A, 0.1% TFA (TFA: trifluoroacetic acid) B, 0.1% TFA/80% CH$_3$CN |
| Eluting Conditions: | Gradient elution of A → B (15%/min.) |

Results of the amino acid sequencing was as shown in FIGS. 1 and 2.

2) Preparation of Genomic DNA.
a) Process for the Extraction of Genomic D-Pantolactone Hydrolase DNA Cultured cells at an anaphase of a logarithmic growth phase were harvested by means of a filtration in vacuo. The cells were placed in liquid nitrogen and finely disrupted using a Waring Blender. The cell mixtures which were made fine to some extent were transferred to a mortar and ground together with the addition of liquid nitrogen. This product was suspended in a 2×CTAB solution (2% CTAB (CTAB: cetyl trimethylammonium bromide; Sigma, USA), 0.1M Tris-HCl (pH 8.0), 1.4M NaCl and 1% PVP (PVP: polyvinylpyrrolidone; Sigma, USA)) kept at 70° C. and incubated at 65° C. for 3–4 hours. The supernatant liquid obtained by centrifugation was successively treated with phenol, phenol/chloroform and chloroform and the resultant solution was then treated with the same volume of isopropanol to precipitate DNA. This DNA paste was washed with 70% ethanol, air-dried and dissolved in a TE buffer (10 mM Tris and 1 mM EDTA; pH 7.8). RNA was decomposed with ribonuclease A and ribonuclease T1. Then the DNA product was successively treated with phenol, phenol/chloroform and chloroform to remove the protein therefrom. The resultant product was treated with the same volume of isopropanol to precipitate DNA. This DNA was washed with 70% ethanol, air-dried and dissolved in a TE buffer to afford a genome sample.

b) Amplification of D-Pantolactone Hydrolase Gene.

Based upon the information on amino acid sequences (FIGS. 1 and 2) of D-pantolactone hydrolase internal peptides, a sense primer corresponding to a sense strand coding for the N-terminal amino acid sequence and an antisense primer corresponding to an antisense strand for the internal peptide sequence were synthesized (FIG. 3).

PCR was carried out under the following conditions using, as a template, a genomic DNA sample of D-pantolactone hydrolase:

The PCR was conducted by the techniques mentioned in the art, for example, in R. Saiki, et al., Science, Vol. 230, pp. 1350 (1985); R. Saiki, et al., Science, Vol. 239, pp. 487 (1988); PCR Technology, Stockton Press (1989); etc.

As a result of the PCR, amplified DNA fragments with about 1 kb were obtained.

| PCR Conditions | |
|---|---|
| Genomic DNA: | 2.5 μg |
| Sense Primer: | 250 pmol (cf. FIG. 3) |
| Antisense Primer: | 250 pmol (cf. FIG. 3) |
| dNTP (2 mM): | 5 μl |
| Tth Polymerase Buffer (× 10): | 5 μl |
| Tth DNA Polymerase (Toyobo, Japan): | 3 units |
| H$_2$O: | |
| Total | 50 μl |

The cycle for amplification including 92° C. for 1 min., 55° C. for 1 min. and 73° C. for 3 min. was repeated 30 times.

The resulting amplified DNA fragments were subjected a sequencing and the disclosed DNA sequence was decoded to an amino acid sequence whereby a portion corresponding to the partial amino acid sequence of the D-pantolactone hydrolase internal peptide was found among the decoded amino acid sequences.

3) Preparation of cDNA.
a) Preparation of mRNA.

Cultured cells were harvested at a prophase of the logarithmic growth phase, immediately frozen with liquid nitrogen, disrupted and subjected to an AGPC (Acid Guanidinium Thiocyanate Phenol Chloroform Method; see, for example, Jikken Igaku, Vol. 15, p. 99 (1991)) to extract total RNA. The resulting total RNA was subjected to an oligo dT-cellulose column (Pharmacia) for purification to afford a mRNA fraction.

b) Preparation of cDNA Library.

The resulting mRNA was used as a template for synthesizing cDNA by a cDNA rapido adaptor ligation module (cDNA synthesis module RPN 1256, 1994; Amersham International PLC) and the cDNA was used for construction of cDNA Libraries.

c) Cloning of D-Pantolactone Hydrolase cDNA.

The cDNA libraries were infected to host *Escherichia coli* cells and positive plaques were selected by means of a plaque hybridization. In the plaque hybridization, probes used for selection were prepared by using about 1 kb fragments containing *Fusarium oxysporum* D-pantolactone hydrolase gene and by labeling the about 1 kb fragments according to a multiprime method. The resulting positive clone was sequenced and the disclosed DNA sequence was decoded to an amino acid sequence whereby it was found that the full length of the above D-pantolactone hydrolase gene was successfully cloned.

As such, the isolated and sequenced DNA has a nucleotide sequence of SEQ ID NO:2. The sequence showing a homology with the amino acid sequence represented by SEQ ID NO:1 encoded by this nucleotide sequence is not present in the Protein Sequence Data Bank of NBRF (National Biomedical Research Foundation). Thus, the DNA having this nucleotide sequence has been found to be entirely novel.

It was found that, in the cDNA where the nucleotides were sequenced, a part of the N-terminal region was lacked and there was no initiation codon therein. Therefore, an initiation codon was artificially incorporated into the cDNA by a PCR technique to construct a vector for expressing the gene (PFLC40E).

Sense and antisense oligonucleotide primers having the restriction enzyme sites as shown in FIG. 4 were synthesized. PCR was carried out utilizing those primers under the following conditions:

The PCR was conducted by the techniques mentioned in the art, for example, in R. Saiki, et al., Science Vol. 230, pp. 1350 (1985); R. Saiki, et al., Science, Vol. 239, pp. 487 (1988); and PCR Technology, Stockton Press (1989).

| PCR Conditions | |
|---|---|
| Total DNA (cDNA): | 10 μg |
| Sense Primer: | 0.1 nmol (cf. FIG. 4) |
| Antisense Primer: | 0.1 nmol (cf. FIG. 4) |
| dNTP (2 mM): | 10 μl |
| Tth Polymerase Buffer (× 10): | 10 μl |
| Tth DNA Polymerase: | 4 units |
| H$_2$O: | |
| Total | 100 μl |

The cycle for amplification including 94° C. for 1 min., 55° C. for 1 min. and 75° C. for 3 min. was repeated 30 times.

The PCR products prepared as such had each restriction enzyme EcoRI and XbaI sites at their both terminals. Therefore, each of them was treated with EcoRI (Takara Shuzo, Japan) and XbaI (Takara Shuzo, Japan) followed by a ligation with pUC18 (Takara Ligation Kit; Takara Shuzo, Japan) whereby the expression vector (PFLC40E) was constructed.

Then said vector was transfected into *E. coli* JM 109 competent cells according to a technique as mentioned in "Molecular Cloning", Second Edition, 1989, edited by J. Sambrook, et al., Cold Spring Harbor Laboratory Press, to transform host cells. The target transformants were selected on a 2×YT medium (1.5% tryptone, 1% yeast extract and 0.5% NaCl) containing 50 mg/liter ampicillin. The transformation was done according to a calcium chloride technique.

The transformant *E. coli* prepared as such was precultured in a test tube containing 10 ml of the above-mentioned 2×YT medium containing 50 mg/liter ampicillin and then the resulting precultured solution (100 μl in total) was used as seed cells for checking culture time, culture temperature and periods for adding isopropyl-β-thiogalacto-pyranoside (IPTG) in 100 ml of main culture broths having the same composition as the preculture broth.

Results of the culture is shown in Table 1.

After the cultivation, the resulting harvested cells were disrupted by ultra-sonication and centrifuged to afford a supernatant. The resultant supernatant was measured in view of D-pantolactone hydrolase activity.

The specific activity was 2.25 U/mg at an optimal condition. Enzymatic activities of the recombinant proteins were assayed in view of D-pantolactone hydrolase under the following conditions:

The enzymatic activity capable of hydrolyzing 1 μmol of D-pantolactone per minute was defined as one unit (U). To 200 μl of 10% D-pantolactone solution in 0.5M PIPES buffer (pH 7.0) was added 50 μl of an enzyme solution and the mixture was made to react at 30° C. for 120 minutes followed by adding 250 μl of 2 mM EDTA in methanol to quench the reaction. After completion of the reaction, the liquid reaction mixture was subjected to an HPLC (Nucleosil 5C$_{18}$ 4.6×150 mm; eluent: 10% methanol; flow rate: 1 ml/minute; detection wavelength: 230 nm) to determine the % hydrolysis. For example, where the % hydrolysis is 1%, the enzymatic activity/ml of the enzyme solution corresponds to $1.6 \times 10^{-2}$ U/ml.

The transformant *E. coli* JM109, transformed with PFLC40E, was cultured in a 2×YT medium. IPTG was added thereto to make its final concentration 2 mM.

TABLE 1

| Time for Supplying IPTG (hr) | Culturing Time (hr) | Culturing Temperature (° C.) | Specific Activity (units/mg) |
| --- | --- | --- | --- |
| 0 (a) | 6 | 28 | 0.86 |
| 0 (a) | 12 | 28 | 1.94 |
| 4 (b) | 7 | 28 | 1.33 |
| 4 (b) | 12 | 28 | 2.25 |
| 0 (a) | 6 | 37 | 1.05 |
| 0 (a) | 12 | 37 | 1.73 |
| 4 (b) | 7 | 37 | 1.31 |
| 4 (b) | 12 | 37 | 1.67 |

(a): IPTG was added to the 2 × YT medium together with the initiation of the culture.
(b): IPTG was added to the 2 × YT medium after four hours from the initiation of the culture.

As a result of an SDS-PAGE, a deep band with an expected molecular weight was detected for an insoluble fraction of the centrifuged precipitate. Therefore, the band was subjected to a blotting and the sample was investigated in view of an N-terminal amino acid sequence by an Edman degradation technique whereby its N-terminal amino acid sequence was found to be identical with that of D-pantolactone hydrolase.

Accordingly, it is likely that, although the recombinant D-pantolactone hydrolase was in part expressed as a soluble form in this *E. coli* expression system for expressing the D-pantolactone hydrolase cDNA, most of the recombinant D-pantolactone hydrolase is expressed as an inclusion body.

The transformant *Escherichia coli*, designated JM109 (EJM-ESE-1), having a recombinant vector (PFLC40E) into which the above-mentioned enzyme D-pantolactone hydrolase gene is integrated has been deposited and stored with the National institute of Bioscience and Human Technology (NIBH), Agency of Industrial Science and Technology, Ministry of International Trade and Industry, Japan, located at 1-3, Higashi 1-chome, Tsukuba-shi, IBARAKI (Zip Code: 305), JAPAN. The transformant *E. coli* JM109 (EJM-ESE-1) has been assigned the Accession Number FERM BP-5638 by NIBH. A request for transferring the original deposit (Accession Number FERM P-15141 deposited on Aug. 30, 1995) to one under the Budapest Treaty was submitted on Aug. 28, 1996.

INDUSTRIAL APPLICABILITY

The present invention discloses gene structures coding for naturally-occurring D-pantolactone hydrolase (such as natural D-pantolactone hydrolase originating in *Fusarium oxysporum*) or for proteins having a substantially equivalent activity thereto. Thus, significant developments can be expected in applications, including uses of host cells which are transformed with DNA containing the nucleotide sequence coding for said protein, processes for the preparation of said protein using said host cells and manufacturing processes for producing D-pantolactone using such proteins and host cells. In addition, it is possible to afford a significant increase in the enzymatic activity by modification of the D-pantolactone hydrolase per se.

What is claimed is:

1. An isolated nucleic acid having a nucleotide sequence coding for a protein having D-pantolactone hydrolase activity, wherein said protein originated from the genus Fusarium and wherein said nucleotide sequence encodes for the protein encoded by the nucleotide sequence of SEQ ID NO:2.

2. An isolated nucleic acid, which has a nucleotide sequence having a portion corresponding to an open reading frame in the nucleotide sequence of SEQ ID NO:2.

3. A vector carrying the nucleic acid according to claims 1 or 2.

4. A transformant wherein the vector according to claim 3 is harbored.

5. A process for producing a protein comprising of a D-pantolactone hydrolase or a salt thereof encoded by the nucleic acid according to claims 1 or 2, which comprises:

culturing a transformant in a nutrient medium suitable for growing said transformant to produce, as a recombinant protein, a protein encoded by the nucleic acid according to claims 1 or 2, wherein the transformant harbors a vector carrying the nucleic acid according to claims 1 or 2.

6. An isolated nucleic acid having a nucleotide sequence coding for a protein of SEQ ID NO: 1 having D-pantolactone hydrolase activity.

7. The nucleic acid according to claim 6, which has a nucleotide sequence having a portion corresponding to an open reading frame in the nucleotide sequence of SEQ ID NO:2.

8. A vector carrying the nucleic acid according to claims 6 or 7.

9. A transformant wherein the vector according to claim 8 is harbored.

10. A process for producing a protein having D-pantolactone hydrolase activity or a salt thereof which comprises:

culturing the transformant according to claim 9 in a nutrient medium suitable for growing said transformant to produce the protein of SEQ ID NO: 1 having D-pantolactone hydrolase activity, or a salt thereof.

11. A process for producing D-pantolaotone which comprises:

carrying out an optical resolution of D, L-pantoclactone in the presence of (i) a protein of SEQ ID NO: 1 having D-pantolactone hydrolase activity or a salt thereof or (ii) the transformant according to claim 9.

* * * * *

UNITED STATES PATENT AND TRADEMARK OFFICE
CERTIFICATE OF CORRECTION

PATENT NO. : 6,794,171 B2  
APPLICATION NO. : 10/133372  
DATED : September 21, 2004  
INVENTOR(S) : Keiji Sakamoto et al.

It is certified that error appears in the above-identified patent and that said Letters Patent is hereby corrected as shown below:

On the title page: Item should read

-- (73) Assignee: Daiichi Fine Chemical Co., Ltd., Takaoka-shi (JP) --

Signed and Sealed this

Twenty-fourth Day of April, 2007

JON W. DUDAS  
*Director of the United States Patent and Trademark Office*

SEQUENCE LISTING

<160> NUMBER OF SEQ ID NOS: 12

<210> SEQ ID NO 1
<211> LENGTH: 380
<212> TYPE: PRT
<213> ORGANISM: Fusarium oxysporum

<220> FEATURE:
<223> OTHER INFORMATION: IFO 5942

<400> SEQUENCE: 1

| | | | | | | | | | | | | | | |
|---|---|---|---|---|---|---|---|---|---|---|---|---|---|---|
| Ala | Lys | Leu | Pro | Ser | Thr | Ala | Gln | Ile | Ile | Asp | Gln | Lys | Ser | Phe | Asn |
| 1 | | | | 5 | | | | | 10 | | | | | 15 | |
| Val | Leu | Lys | Asp | Val | Pro | Pro | Ala | Val | Ala | Asn | Asp | Ser | Leu | Val |
| | | | 20 | | | | 25 | | | | | 30 | | |
| Phe | Thr | Trp | Pro | Gly | Val | Thr | Glu | Glu | Ser | Leu | Val | Glu | Lys | Pro | Phe |
| | | 35 | | | | | 40 | | | | | 45 | | | |
| His | Val | Tyr | Asp | Glu | Glu | Phe | Tyr | Asp | Val | Ile | Gly | Lys | Asp | Pro | Ser |
| 50 | | | | | 55 | | | | | 60 | | | | | |
| Leu | Thr | Leu | Ile | Ala | Thr | Ser | Asp | Thr | Asp | Pro | Ile | Phe | His | Glu | Ala |
| 65 | | | | | 70 | | | | | 75 | | | | | 80 |
| Val | Val | Trp | Tyr | Pro | Pro | Thr | Glu | Glu | Val | Phe | Phe | Val | Gln | Asn | Ala |
| | | | | 85 | | | | | 90 | | | | | 95 | |
| Gly | Ala | Pro | Ala | Ala | Gly | Thr | Gly | Leu | Asn | Lys | Ser | Ser | Ile | Ile | Gln |
| | | | 100 | | | | | 105 | | | | | 110 | | |
| Lys | Ile | Ser | Leu | Lys | Glu | Ala | Asp | Ala | Val | Arg | Lys | Gly | Lys | Gln | Asp |
| | | 115 | | | | | 120 | | | | | 125 | | | |
| Glu | Val | Lys | Val | Thr | Val | Val | Asp | Ser | Asn | Pro | Gln | Val | Ile | Asn | Pro |
| 130 | | | | | 135 | | | | | 140 | | | | | |
| Asn | Gly | Gly | Thr | Tyr | Tyr | Lys | Gly | Asn | Ile | Ile | Phe | Ala | Gly | Glu | Gly |
| 145 | | | | | 150 | | | | | 155 | | | | | 160 |
| Gln | Gly | Asp | Asp | Val | Pro | Ser | Ala | Leu | Tyr | Leu | Met | Asn | Pro | Leu | Pro |
| | | | | 165 | | | | | 170 | | | | | 175 | |
| Pro | Tyr | Asn | Thr | Thr | Thr | Leu | Leu | Asn | Asn | Tyr | Phe | Gly | Arg | Gln | Phe |
| | | | 180 | | | | | 185 | | | | | 190 | | |
| Asn | Ser | Leu | Asn | Asp | Val | Gly | Ile | Asn | Pro | Arg | Asn | Gly | Asp | Leu | Tyr |
| | | | 195 | | | | | 200 | | | | | 205 | | |
| Phe | Thr | Asp | Thr | Leu | Tyr | Gly | Tyr | Leu | Gln | Asp | Phe | Arg | Pro | Val | Pro |
| | | 210 | | | | | 215 | | | | | 220 | | | |
| Gly | Leu | Arg | Asn | Gln | Val | Tyr | Arg | Tyr | Asn | Phe | Asp | Thr | Gly | Ala | Val |
| 225 | | | | | 230 | | | | | 235 | | | | | 240 |
| Thr | Val | Val | Ala | Asp | Asp | Phe | Thr | Leu | Pro | Asn | Gly | Ile | Gly | Phe | Gly |
| | | | | 245 | | | | | 250 | | | | | 255 | |
| Pro | Asp | Gly | Lys | Lys | Val | Tyr | Val | Thr | Asp | Thr | Gly | Ile | Ala | Leu | Gly |
| | | | 260 | | | | | 265 | | | | | 270 | | |
| Phe | Tyr | Gly | Arg | Asn | Leu | Ser | Ser | Pro | Ala | Ser | Val | Tyr | Ser | Phe | Asp |
| | | 275 | | | | | 280 | | | | | 285 | | | |
| Val | Asn | Gln | Asp | Gly | Thr | Leu | Gln | Asn | Arg | Lys | Thr | Phe | Ala | Tyr | Val |
| | 290 | | | | | 295 | | | | | 300 | | | | |
| Ala | Ser | Phe | Ile | Pro | Asp | Gly | Val | His | Thr | Asp | Ser | Lys | Gly | Arg | Val |
| 305 | | | | | 310 | | | | | 315 | | | | | 320 |
| Tyr | Ala | Gly | Cys | Gly | Asp | Gly | Val | His | Val | Trp | Asn | Pro | Ser | Gly | Lys |
| | | | | 325 | | | | | 330 | | | | | 335 | |
| Leu | Ile | Gly | Lys | Ile | Tyr | Thr | Gly | Thr | Val | Ala | Ala | Asn | Phe | Gln | Phe |
| | | | 340 | | | | | 345 | | | | | 350 | | |
| Ala | Gly | Lys | Gly | Arg | Met | Ile | Ile | Thr | Gly | Gln | Thr | Lys | Leu | Phe | Tyr |
| | | 355 | | | | | 360 | | | | | 365 | | | |
| Val | Thr | Leu | Gly | Ala | Ser | Gly | Pro | Lys | Leu | Tyr | Asp |
| | 370 | | | | | 375 | | | | | 380 |

<210> SEQ ID NO 2

<211> LENGTH: 1229
<212> TYPE: DNA
<213> ORGANISM: Fusarium oxysporum
<220> FEATURE:
<223> OTHER INFORMATION: IFO 5942
<220> FEATURE:
<221> NAME/KEY: CDS
<222> LOCATION: (12)..(1151)

<400> SEQUENCE: 2

```
ccatggtggc t gct aag ctt cct tct acg gct cag att att gat cag aag        50
            Ala Lys Leu Pro Ser Thr Ala Gln Ile Ile Asp Gln Lys
              1               5                  10 tcg ttc aat gtc ttg aag gat gtg cca cct cct gca gtg gcc aat gac        98
Ser Phe Asn Val Leu Lys Asp Val Pro Pro Pro Ala Val Ala Asn Asp
         15                  20                  25 tct ctg gtg ttc act tgg cct ggt gta act gag gag tct ctt gtt gag       146
Ser Leu Val Phe Thr Trp Pro Gly Val Thr Glu Glu Ser Leu Val Glu
 30                  35                  40                  45 aag cct ttc cat gtc tac gat gaa gag ttt tac gat gta att gga aaa       194
Lys Pro Phe His Val Tyr Asp Glu Glu Phe Tyr Asp Val Ile Gly Lys
                 50                  55                  60 gac ccc tct ttg acc ctc atc gca aca tcg gac acc gac cca atc ttc       242
Asp Pro Ser Leu Thr Leu Ile Ala Thr Ser Asp Thr Asp Pro Ile Phe
             65                  70                  75 cat gag gct gtc gta tgg tat cct cct act gaa gag gtg ttc ttt gtg       290
His Glu Ala Val Val Trp Tyr Pro Pro Thr Glu Glu Val Phe Phe Val
         80                  85                  90 cag aat gct ggc gct cct gcc gca ggc act ggc ttg aac aag tct tcc       338
Gln Asn Ala Gly Ala Pro Ala Ala Gly Thr Gly Leu Asn Lys Ser Ser
 95                 100                 105 atc att cag aag att tcc ctc aag gag gcc gat gct gtt cgc aag ggc       386
Ile Ile Gln Lys Ile Ser Leu Lys Glu Ala Asp Ala Val Arg Lys Gly
110                 115                 120                 125 aag cag gat gag gtc aag gtc aca gtt gtt gac tcg aac cct cag gtt       434
Lys Gln Asp Glu Val Lys Val Thr Val Val Asp Ser Asn Pro Gln Val
                130                 135                 140 atc aac cca aat ggt ggt act tac tac aag ggc aac atc atc ttc gct       482
Ile Asn Pro Asn Gly Gly Thr Tyr Tyr Lys Gly Asn Ile Ile Phe Ala
            145                 150                 155 ggt gag ggc caa ggc gac gat gtt ccc tct gcg ctg tac ctc atg aac       530
Gly Glu Gly Gln Gly Asp Asp Val Pro Ser Ala Leu Tyr Leu Met Asn
        160                 165                 170 cct ctc cct cct tac aac acc acc acc ctt ctc aac aac tac ttc ggt       578
Pro Leu Pro Pro Tyr Asn Thr Thr Thr Leu Leu Asn Asn Tyr Phe Gly
175                 180                 185 cgc cag ttc aac tcc ctc aac gac gtc ggt atc aac ccc agg aac ggt       626
Arg Gln Phe Asn Ser Leu Asn Asp Val Gly Ile Asn Pro Arg Asn Gly
190                 195                 200                 205 gac ctg tac ttc acc gat acc ctc tac gga tat ctc caa gac ttc cgt       674
Asp Leu Tyr Phe Thr Asp Thr Leu Tyr Gly Tyr Leu Gln Asp Phe Arg
                210                 215                 220 cct gtt cct ggt ctg cga aac cag gtc tat cgt tac aac ttt gac act       722
Pro Val Pro Gly Leu Arg Asn Gln Val Tyr Arg Tyr Asn Phe Asp Thr
            225                 230                 235 ggc gct gtc act gtt gtc gct gat gac ttt acc ctt ccc aac ggt att       770
Gly Ala Val Thr Val Val Ala Asp Asp Phe Thr Leu Pro Asn Gly Ile
        240                 245                 250 ggc ttt ggc ccc gac ggc aag aag gtt tat gtc acc gac act ggc atc       818
Gly Phe Gly Pro Asp Gly Lys Lys Val Tyr Val Thr Asp Thr

| | | | | | | | | | | | | | | |
|---|---|---|---|---|---|---|---|---|---|---|---|---|---|---|
| gct | ctc | ggt | ttc | tac | ggt | cgc | aac | ctc | tct | tct | ccc | gct | tct | gtt | tac | 866 |
| Ala | Leu | Gly | Phe | Tyr | Gly | Arg | Asn | Leu | Ser | Ser | Pro | Ala | Ser | Val | Tyr |
| 270 | | | | 275 | | | | 280 | | | | 285 | | | |

```
gct ctc ggt ttc tac ggt cgc aac ctc tct tct ccc gct tct gtt tac      866
Ala Leu Gly Phe Tyr Gly Arg Asn Leu Ser Ser Pro Ala Ser Val Tyr
270             275                 280                 285 tct ttc gac gtg aac cag gac ggt act ctt cag aac cgc aag acc ttt      914
Ser Phe Asp Val Asn Gln Asp Gly Thr Leu Gln Asn Arg Lys Thr Phe
                290                 295                 300 gct tat gtt gcc tca ttc atc ccc gat ggt gtc cac act gac tcc aag      962
Ala Tyr Val Ala Ser Phe Ile Pro Asp Gly Val His Thr Asp Ser Lys
            305                 310                 315 ggt cgt gtt tat gct ggc tgc ggt gat ggt gtc cat gtc tgg aac ccc     1010
Gly Arg Val Tyr Ala Gly Cys Gly Asp Gly Val His Val Trp Asn Pro
        320                 325                 330 tct ggc aag ctc atc ggc aag atc tac acc gga acg gtt gct gct aac     1058
Ser Gly Lys Leu Ile Gly Lys Ile Tyr Thr Gly Thr Val Ala Ala Asn
335                 340                 345 ttc cag ttt gct ggt aag gga agg atg ata att act gga cag acg aag     1106
Phe Gln Phe Ala Gly Lys Gly Arg Met Ile Ile Thr Gly Gln Thr Lys
350                 355                 360                 365 ttg ttc tat gtc act cta ggg gct tcg ggt ccc aag ctc tat gat         1151
Leu Phe Tyr Val Thr Leu Gly Ala Ser Gly Pro Lys Leu Tyr Asp
                370                 375                 380 tagaaatgtt cacttctcta tacttacata gataatacat ggcatttgac ttttgaaaaa   1211
aaaaaaaaaa aaccatgg                                                 1229

<210> SEQ ID NO 3
<211> LENGTH: 10
<212> TYPE: PRT
<213> ORGANISM: Fusarium oxysporum
<220> FEATURE:
<223> OTHER INFORMATION: IFO 5942
<220> FEATURE:
<221> NAME/KEY: MOD_RES
<222> LOCATION: (5)
<223> OTHER INFORMATION: Uncertain residue

<400> SEQUENCE: 3

Gly Arg Met Ile Xaa Thr Gly Gln Thr Lys
1               5                   10

<210> SEQ ID NO 4
<211> LENGTH: 19
<212> TYPE: PRT
<213> ORGANISM: Fusarium oxysporum
<220> FEATURE:
<223> OTHER INFORMATION: IFO 5942
<220> FEATURE:
<221> NAME/KEY: MOD_RES
<222> LOCATION: (7)
<223> OTHER INFORMATION: Uncertain residue

<400> SEQUENCE: 4

Gly Arg Val Tyr Ala Gly Xaa Gly Asp Gly Val His Val Trp Asn Pro
1               5                   10                  15

Ser Gly Lys

<210> SEQ ID NO 5
<211> LENGTH: 33
<212> TYPE: PRT
<213> ORGANISM: Fusarium oxysporum
<220> FEATURE:
<223> OTHER INFORMATION: IFO 5942
<220> FEATURE:
<221> NAME/KEY: MOD_RES
<222> LOCATION: (33)
<223> OTHER INFORMATION: Uncertain residue
```

```
<400> SEQUENCE: 5

Gly Asn Ile Ile Phe Ala Gly Glu Gly Gln Gly Asp Asp Val Pro Ser
 1               5                  10                  15

Ala Leu Tyr Leu Met Asn Pro Leu Pro Tyr Asn Thr Thr Thr Leu
            20                  25                  30

Xaa

<210> SEQ ID NO 6
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Phe His Val Tyr Asp Glu Glu Phe Tyr Asp
 1               5                  10

<210> SEQ ID NO 7
<211> LENGTH: 38
<212> TYPE: DNA
<213> ORGANISM: Artificial Sequence
<220> FEATURE:
<223> OTHER INFORMATION: Description of Artificial Sequence: Primer

<400> SEQUENCE: 7
aaaagcttyc acgtctayga ygargartty taygaygt                           38

<210> SEQ ID NO 8
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Pro Asn Trp Val His Val Gly Asp
 1               5

<210> SEQ ID NO 9
<211> LENGTH: 35
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (21)
<223> OTHER INFORMATION: a, t, c or g
<220> FEATURE:
<221> NAME/KEY: modified_base
<222> LOCATION: (27)
<223> OTHER INFORMATION: a, t, c or g
<220> FEATURE:
<221> NAME/KEY: modified_base
<222> LOCATION: (30)
<223> OTHER INFORMATION: a, t, c or g

<400> SEQUENCE: 9
ggcttgctgc agggrttcca nacrtgnacn ccrtc                              35

<210> SEQ ID NO 10
<211> LENGTH: 51
<212> TYPE: DNA
```

```
<213> ORGANISM: Artificial Sequence
<220> FEATURE:
<223> OTHER INFORMATION: Description of Artificial Sequence: Primer
<220> FEATURE:
<221> NAME/KEY: CDS
<222> LOCATION: (25)..(51)

<400> SEQUENCE: 10
gtgaattcta aggaggaata ggtg atg gct aag ctt cct tct acg gct cag        51
                          Met Ala Lys Leu Pro Ser Thr Ala Gln
                           1               5

<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Met Ala Lys Leu Pro Ser Thr Ala Gln
 1               5

<210> SEQ ID NO 12
<211> LENGTH: 36
<212> TYPE: DNA
<213> ORGANISM: Artificial Sequence
<220> FEATURE:
<223> OTHER INFORMATION: Description of Artificial Sequence: Primer

<400> SEQUENCE: 12
gtaagtctag agaagtgaac atttctaatc atagag        36
```